(12) United States Patent
Simard et al.

(10) Patent No.: US 8,277,785 B2
(45) Date of Patent: Oct. 2, 2012

(54) COSMETIC COMPOSITIONS WITH ENCAPSULATED PIGMENTS AND A METHOD FOR USING

(75) Inventors: Claude C. Simard, Sparrowbush, NY (US); Arvind N. Shah, Suffern, NY (US)

(73) Assignee: Avon Products, Inc., New York, NY (US)

( * ) Notice: Subject to any disclaimer, the term of this patent is extended or adjusted under 35 U.S.C. 154(b) by 934 days.

(21) Appl. No.: 11/301,421

(22) Filed: Dec. 13, 2005

(65) Prior Publication Data

US 2007/0134180 A1    Jun. 14, 2007

(51) Int. Cl.
*A61K 8/25* (2006.01)
(52) U.S. Cl. .............. 424/63; 424/401; 424/61
(58) Field of Classification Search .......... 424/63, 424/401, 61
See application file for complete search history.

(56) References Cited

U.S. PATENT DOCUMENTS

| | | | |
|---|---|---|---|
| 2,885,366 A | 5/1959 | Iler | 252/313 |
| 3,410,708 A | 11/1968 | McGinnis | 106/300 |
| 3,437,502 A | 4/1969 | Werner | 106/300 |
| 3,591,398 A | 7/1971 | Angerman | 106/300 |
| 4,199,370 A | 4/1980 | Brand | 106/300 |
| 5,382,433 A | 1/1995 | Pahlck et al. | |
| 6,113,682 A | 9/2000 | Shin et al. | 106/446 |
| 6,355,260 B1 | 3/2002 | Tanaka et al. | |
| 6,627,314 B2 | 9/2003 | Matyjaszewski et al. | |
| 6,648,958 B2 | 11/2003 | Anselmann et al. | 106/442 |
| 7,052,777 B2 | 5/2006 | Brotzman, Jr. et al. | |
| 2002/0071948 A1* | 6/2002 | Duff et al. | 428/323 |
| 2003/0118530 A1 | 6/2003 | O'Brien et al. | |
| 2004/0018161 A1* | 1/2004 | Shah et al. | 424/63 |
| 2005/0069704 A1* | 3/2005 | Rathschlag et al. | 428/402.21 |
| 2006/0257662 A1 | 11/2006 | Bujard et al. | |

FOREIGN PATENT DOCUMENTS

| | | |
|---|---|---|
| EP | 0581651 | 2/1994 |
| JP | 60-228406 A | 11/1985 |
| JP | 2003-3089 A | 1/2003 |
| WO | WO 98/06791 | 2/1998 |
| WO | 2005/115309 A2 | 12/2005 |
| WO | 2006/085957 A2 | 8/2006 |

OTHER PUBLICATIONS

International Search Report dated Mar. 5, 2007.
3 M Product Information—NOVEC 1230 Fire Protection Fluid, 8 pps., Sep. 2003.
3 M Product Information—NOVEC Engineered Fluid HFE-7000, 7 pps., Jul. 2001.
3 M Product Information—NOVEC Engineered Fluid HFE-7100 for Heat Transfer, 7 pps., Jan. 2002.

* cited by examiner

*Primary Examiner* — San-Ming Hui
*Assistant Examiner* — Kathrien Cruz
(74) *Attorney, Agent, or Firm* — Charles J. Zeller; Joan M McGillycuddy; David M Joyal

(57) ABSTRACT

There is a pigmented cosmetic composition. The composition has a cosmetically acceptable vehicle, a cosmetic active, and a plurality of encapsulated pigment particles. The particles have an encapsulant and an entrapped pigment within the encapsulant. The encapsulant has silicon dioxide and exhibits a refractive index of about 1.4 to about 1.6.

9 Claims, No Drawings

COSMETIC COMPOSITIONS WITH ENCAPSULATED PIGMENTS AND A METHOD FOR USING

BACKGROUND OF THE INVENTION

1. Field of the Invention

The invention relates to a cosmetic composition having encapsulated pigments. The invention further relates to a method for imparting a cosmetic effect on a topical surface.

2. Description of the Related Art

Cosmetic compositions commonly employ pigments as masking agents to improve the intrinsic visual appearance of the compositions and/or to impart a particular appearance upon topical application.

Pigmented cosmetic compositions frequently impart an opaque and artificial appearance to the skin. The opaque and artificial appearance results from the difference in refractivity between the pigments and the skin. Pigments commonly exhibit an index of refractivity in excess of 2. Skin, on the other hand, typically exhibits an index of refractivity of about 1.4 to 1.5.

One means employed in the cosmetic art to create a less opaque and more natural-looking appearance is to incorporate pearlescents instead of pigments. However, pearlescents are relatively expensive and oftentimes provide an artificial appearance to the skin. Accordingly, it is desirable to minimize their use.

It would be desirable to have a pigmented cosmetic composition that imparts a visual appearance that is less opaque, i.e., more translucent, and more natural-looking.

SUMMARY OF THE INVENTION

It is an object of the present invention to provide a pigmented cosmetic composition that is less opaque and more natural-looking.

According to these and other objects of the invention, there is provided a pigmented cosmetic composition. The composition has a cosmetically acceptable vehicle, an active ingredient, and a plurality of encapsulated pigment particles. The particles are made up of an encapsulant and an entrapped pigment within the encapsulant. The encapsulant has silicon dioxide (silica) and exhibits a refractive index of about 1.4 to about 1.6.

DETAILED DESCRIPTION OF THE INVENTION

It was surprisingly found that there could be a pigmented cosmetic composition that is less opaque and more natural-looking. It was further surprisingly found that there could be a method for imparting a cosmetic effect to a topical surface.

The cosmetic composition has a plurality of encapsulated pigment particles therein to impart a visual effect of color with respect to the composition itself and/or upon topical application to the topical surface. The visual effect is less opaque and more natural-looking compared to compositions having non-encapsulated pigment particles.

An encapsulated pigment particle is made up of an encapsulant and an entrapped pigment particles within the encapsulant. The encapsulant essentially covers the entire surface of the pigment particle and takes the form of a coating or layering.

The encapsulated pigment particles impart a less opaque and more natural-looking visual appearance since they have a different refractivity than pigment particles alone (without encapsulation). Silicon dioxide, the material predominantly present in the encapsulant, exhibits an index of refractivity of about 1.4 to about 1.6, which is comparable to the index of refractivity of the skin.

The composition has one or more pigments therein. Useful pigments include any known in the cosmetic art. Examples of useful pigments include titanium dioxide, zinc oxide, iron oxide, chromium oxide, ferric blue, carbon black, mica, manganese violet, ultramarines, and combinations thereof. The pigments can be of any shape, although spherical is preferred. Preferred mean average particle sizes are about 10 microns or less and more preferred sizes are about 1 micron or less.

The pigments can be present in the composition in an amount of 1 wt % to about 25 wt % of the total weight of the composition, and preferably in an amount of about 1 wt % to about 15 wt % based on the total weight of the composition.

The encapsulant refers to the covering or coating that encloses or encapsulates the pigment. The encapsulant substantially prevents direct communication or contact between the pigment and the greater composition. The encapsulant is made up substantially of silicon dioxide, although minor amounts, i.e., less than 10 wt % (based on total composition weight) of other substances are possible so long as a desirable degree of refractivity, i.e., an index of refraction of about 1.4 to about 1.6, is maintained.

If the average thickness of the encapsulant is too thin, then some areas of the particles may remain exposed and non-encapsulated. If the average thickness of the encapsulant is too thick, the color of the pigment will be diminished and coverage of the skin will be compromised.

The amount of encapsulant employed to encapsulate pigment particles is functionally that amount of encapsulant that provides a refractive index for the encapsulated pigment particle of the invention that approximates the refractive index of the skin, namely, between about 1.4 and 1.6. Typically, the encapsulant employed is about 1 to about 20 wt %, preferably about 3 to about 12 wt % of the total weight of the encapsulated pigment particles.

Since the encapsulated pigment particles have a more translucent and natural-looking appearance, they can be substituted in whole or in part for more expensive pearlescents frequently found in prior art cosmetic compositions.

The pigments can be encapsulated with silicon dioxide (silica) by any means known in the art. For example, the sol-gel glass process can be used to provide the coating of the silica on the core pigment particle. In this process the silica precursor is reacted in a series of hydrolysis and polymerization reactions to form a colloidal suspension, or sol, which is then precipitated onto the pigment core to provide a thin film coating of silica on the core pigment particle. See Brinker and Scherer, The Physics and Chemistry of Sol-Gel Processing (1990). Mention may also be made of U.S. Pat. Nos. 3,410,708; 3,437,502; 3,591,398; and 4,199,370, which disclose methods for imparting a silica coating via use of aqueous sodium silicate and pH adjustment, known generally in the art as the sol-gel process. The aforementioned text and patents are incorporated herein by reference.

The active ingredient can take the form of any compound that imparts a cosmetic, functional, and/or medicinal effect to the topical surface or improves the aesthetic appearance thereof. Representative compounds include the following: but are not limited to, anesthetics, anti-allergenics, antifungals, antimicrobials, anti-inflammatories, antiseptics, astringents, barrier agents, botanical extracts, chelating agents, de-pigmenting agents, detergents/cleansers, de-wrinkling agents, emollients, exfoliants, film formers, firming agents, fragrances, humectants, insect repellents, lubricants, moisturizers, pharmaceutical agents, pigmenting agents, preservatives, skin protectants, skin penetration enhancers, stabilizers, sunscreen agents, surfactants, thickeners, vitamins, and any combinations thereof.

The composition has an active ingredient in an amount sufficient to impart a cosmetic/functional/medicinal effect (referred to collectively as cosmetic effect) to the topical surface. The amount will vary considerably depending on the type of effect desired and the properties of the active ingredient. The active ingredient will typically be present at about 0.001 to about 95 wt % and more typically present at about 0.001 to about 50 wt %, and most typically present at about 0.001 to about 25 wt % based on the total weight of the topical composition.

The composition can assume any product form known in the art. Useful product forms include solution, lotion, paste, loose powder, pressed powder, cream, stick, gel, mousse, mask, bead, and pomade. The composition can be aqueous or non-aqueous. The composition may take the form of a solution, dispersion, suspension, or emulsion. Emulsions may be, for example, oil/water, water/oil, silicon/water, water/silicon, wax/water, or water/wax.

The composition may employ a variety of cosmetically acceptable vehicles or carriers. Useful vehicles include, but are not limited to, water, lower alcohols, polyhydric alcohols, fatty acids, fatty alcohols, fatty ethers, fatty esters, $C_{10}$ to $C_{24}$ alkanes, volatile and nonvolatile and linear and cyclic silicones, mineral oils, other hydrocarbons such as isoparaffins, and combinations thereof.

In another aspect of the invention, the composition can be applied to any topical surface to impart a desired cosmetic effect thereto. Useful topical surfaces include skin, hair, lips, and nails. Any area of the skin, such as the hands and face, may be treated. The composition may be applied as often and/or as long as needed or desired. For instance, the composition may be applied one or more times per day for as little as a day, a week or more, or two weeks or more.

The following are examples of the invention. Unless otherwise indicated below, all parts, percentages, and proportions are by weight.

EXAMPLES

Example 1

Liquid Makeup—Oil in Water

| | Phase A: |
|---|---|
| 63.2% | Demineralized Water |
| 0.7% | Magnesium Aluminum Silicate |
| 0.1% | Xanthan Gum |
| 0.3% | Methylparaben |
| 0.1% | Tetrasodium EDTA |
| 7.0% | Butylene Glycol |
| | Phase B: |
| 7.0% | Titanium Dioxide - Encapsulated in Silica* |
| 1.0% | Iron Oxide-Yellow - Encapsulated in Silica* |
| 0.5% | Cosmetic Red Oxide - Encapsulated in Silica* |
| 0.1% | Iron Oxide-Black - Encapsulated in Silica* |
| 2.0% | Silica 2-20 Micro Sphere Mss 5 |
| | Phase C: |
| 1.0% | Steareth-21 |
| 4.0% | Ethylhexyl Palmitate |
| 0.5% | Steareth-2 |
| 0.5% | Glyceryl Monostearate |
| 7.0% | Mineral Oil |
| 5.0% | Phenyl Trimethicone |
| 100.0% | |

Procedure:
 1. Premix Phase A in homogenizer at 70° C.
 2. Add Phase B and mix in homogenizer at high speed
 3. Premix Phase C and heat to 70° C.
 4. Add Phase C to Phase AB in homogenizer at 70° C.
 5. Cool to 30° C.

Directions:
 Apply evenly with fingertips to cover imperfections, even out skin tone, and provide a natural finish.

Example 2

Liquid Makeup—Water in Silicone

| | Phase A: |
|---|---|
| 1.0% | Cetyl Dimethicone Copolyol |
| 5.0% | Phenyl Trimethicone |
| 20.0% | Cyclomethicone-Pentamer |
| 1.0% | PEG/PPG - 18/18 Dimethicone |
| | Phase B: |
| 8.0% | Titanium Dioxide - Encapsulated in Silica* |
| 1.4% | Iron Oxide-Yellow - Encapsulated in Silica* |
| 0.4% | Iron Oxide-Red- Encapsulated in Silica* |
| 0.2% | Iron Oxide -Black - Encapsulated in Silica* |
| 1.0% | Nylon Powder-Spherical |
| | Phase C: |
| 59.5% | Demineralized Water |
| 2.0% | Butylene Glycol |
| 1.0% | Sodium Chloride |
| 0.2% | Methylparaben |
| 0.3% | Imidazolidinyl Urea |
| 100.0% | |

Procedure:
 1. Premix Phase A in homogenizer at room temperature.
 2. Add Phase B and mix in homogenizer at high speed
 3. Premix Phase C and heat to dissolve solids and cool to room temperature.
 4. Add Phase C to Phase AB in homogenizer Directions:
 Apply evenly with fingertips to cover imperfections, even out skin tone, and provide a natural finish.

Example 3

Cream to Powder Foundation

| | Phase A: |
|---|---|
| 45.2% | Mineral Oil |
| 14.0% | Diisopropyl Dimerate |
| 8.0% | Carnauba Wax |
| 5.0% | Beeswax |
| 3.0% | Glyceryl Tribehenate |
| 6.0% | Ethylhexyl-Methoxycinnamate |

| -continued | |
|---|---|
| 2.0% | Cetyl Ricinoleate |
| 0.2% | Propylparaben |
| | Phase B: |
| 5.0% | Nylon Powder - Extra Fine |
| 2.0% | Mica |
| 6.6% | Titanium Dioxide - Encapsulated in Silica* |
| 2.0% | Iron Oxide- Yellow - Encapsulated in Silica* |
| 0.7% | Iron Oxide- Red - Encapsulated in Silica* |
| 0.3% | Iron Oxide- Black - Encapsulated in Silica* |
| 100.0% | |

Procedure:
1. Premix Phase A with Propeller mixer at 70° C.
2. Add Phase B and mix in homogenizer at high speed
3. Pour at 60° C.-70° C. in pan and cool to room temp.

Directions:
Apply evenly with sponge or fingertips to cover imperfections, even out skin tone, and provide a natural finish.

Example 4

Pressed Face Powder

| Phase A: | |
|---|---|
| 27.17% | Talc |
| 10.0% | Zinc Stearate |
| 10.0% | Kaolin |
| 7.5% | Calcium Silicate |
| 3.0% | Corn Starch |
| 15.0% | Mica |
| 0.2% | Propylparaben |
| 11.0% | Titanium Dioxide - Encapsulated in Silica* |
| 3.5% | Iron Oxide-Yellow - Encapsulated in Silica* |
| 0.86% | Iron Oxide-Red - Encapsulated in Silica* |
| 0.42% | Iron Oxide-Black - Encapsulated in Silica* |
| | Phase B: |
| 1.0% | Dimethicone 50 Cst |
| 1.0% | Sorbitan Sesquioleate |
| 3.5% | Squalane |
| 100.0% | |

Procedure:
1. Pre-grind phase A using micropulverizer
2. Add phase B slowly to Phase A using ribbon blender
3. Press in pans Directions:
Apply evenly with sponge applicator for a natural finish.

Example 5

Stick Foundation

| Phase A: | |
|---|---|
| 28.0% | Phenyl Trimethicone |
| 25.0% | $C_{12-15}$ Alkyl Ethylhexanoate |
| 12.8% | Polyethylene Wax-180 cps |
| 20.00% | Aluminum Starch Octenylsuccinate |
| 3.0% | Mica |
| | Phase B: |
| 8.8% | Titanium Dioxide - Encapsulated in Silica* |

| -continued | |
|---|---|
| 1.8% | Iron Oxide -Yellow - Encapsulated in Silica* |
| 0.4% | Iron Oxide-Red - Encapsulated in Silica* |
| 0.2% | Iron Oxide-Black - Encapsulated in Silica* |
| 100.0% | |

Procedure:
1. Premix Phase A with Propeller mixer at 80° C.-90° C.
2. Add Phase B and mix in homogenizer at high speed
3. Pour at 60° C.-70° C. in pan and cool to room temperature.

Directions:
Dab on, then blend well with fingertips to cover imperfections, even out skin tone, and provide a natural finish.

Example 6

Cream Souffle Makeup—Oil in Water

| Phase A: | |
|---|---|
| 46.8% | Demineralized Water |
| 0.8% | Magnesium Aluminum Silicate |
| 0.2% | Xanthan Gum |
| 0.3% | Methylparaben |
| 1.0% | Triethanolamine 99% |
| 10.0% | Butylene Glycol |
| | Phase B: |
| 6.5% | Titanium Dioxide - Encapsulated in Silica* |
| 1.0% | Iron Oxide-Yellow - Encapsulated in Silica* |
| 0.3% | Cosmetic Red Oxide - Encapsulated in Silica* |
| 0.3% | Iron Oxide-Black - Encapsulated in Silica* |
| | Phase C: |
| 7.5% | Ethylhexyl Palmitate |
| 12.0% | Mineral Oil |
| 2.20% | Stearic Acid |
| 2.00% | PEG-40 Stearate |
| 1.5% | Steareth-2 |
| 5.0% | Candelilla Wax |
| 2.5% | Glyceryl Monostearate |
| 0.1% | Ethylparaben |
| 100.0% | |

Procedure:
1. Premix Phase A in homogenizer at 70° C.
2. Add Phase B and mix in homogenizer at high speed
3. Premix Phase C and heat to 70° C.
4. Add Phase C to Phase AB in homogenizer at 70° C.
5. Cool to 30° C.

Directions:
Dot on with fingertips. Blend evenly to cover imperfections, even out skin tone, and provide a natural finish.

Titanium Dioxide—Encapsulated in Silica DITTANY-TRI-77891

Iron Oxide-Yellow—Encapsulated in Silica DITTANY-Y-77492

Iron Oxide-Red—Encapsulated in Silica DITTANY-R-77491

Iron Oxide-Black—Encapsulated in Silica DITTANY-B-77499

*DITTANY is a tradename of US Cosmetics Corp.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method of imparting a cosmetic effect of a natural-looking cosmetic effect to skin or lips, comprising topically applying to the skin or lips a cosmetic composition comprising:
a cosmetically acceptable vehicle and a plurality of spherical iron oxide pigment particles encapsulated by a layer of silicon dioxide enclosing the iron oxide pigment particle, wherein the silicon dioxide encapsulant is about 3 wt % to about 12 wt % by weight of the encapsulated iron oxide pigment particles.

2. The method of claim 1, wherein the encapsulated spherical iron oxide pigment particles are present from about 1 wt % to about 15 wt % by weight of the composition.

3. The method of claim 1, wherein the spherical iron oxide pigment particles are present in an amount of from about 1 wt % to about 15 wt % by weight of the composition.

4. The method of claim 1, wherein the composition is applied to lips.

5. The method of claim 1, wherein the composition is applied to the skin.

6. The method of claim 1, wherein the composition is non-pearlescent.

7. The method of claim 1, further comprising an active ingredient.

8. The method of claim 7, wherein the active agent is selected from the group consisting of anesthetics, anti-allergenics, anti-inflammatories, botanical agents, de-pigmenting agents, de-wrinkling agents, emollients, exfoliants, fragrances, humectants, lubricants, moisturizers, skin penetration enhancers, sunscreen agents, surfactants, vitamins, and combinations thereof.

9. A method of imparting a cosmetic effect of a natural-looking cosmetic effect to skin or lips, comprising topically applying to the skin or lips a cosmetic composition comprising:
a cosmetically acceptable vehicle and a plurality of spherical iron oxide pigment particles encapsulated by a layer of silicon dioxide enclosing the iron oxide pigment particle, wherein the silicon dioxide encapsulant is about 3 wt % to about 12 wt % by weight of the encapsulated iron oxide pigment particles,
wherein the spherical iron oxide pigment particles have a mean average particle size of from about 1 micron to about 10 microns.

* * * * *